(12) United States Patent
Shvartsman et al.

(10) Patent No.: US 9,675,271 B2
(45) Date of Patent: Jun. 13, 2017

(54) SYSTEMS AND METHODS FOR RADIOTHERAPY WITH MAGNETIC RESONANCE IMAGING

(71) Applicant: ViewRay, Incorporated, Oakwood Village, OH (US)

(72) Inventors: Shmaryu M. Shvartsman, Cleveland, OH (US); James F. Dempsey, Chagrin Falls, OH (US); David Nicolay, Cleveland, OH (US)

(73) Assignee: ViewRay Technologies, Inc., Oakwood Village, OH (US)

( * ) Notice: Subject to any disclaimer, the term of this patent is extended or adjusted under 35 U.S.C. 154(b) by 349 days.

(21) Appl. No.: 13/801,680

(22) Filed: Mar. 13, 2013

(65) Prior Publication Data

US 2014/0275963 A1  Sep. 18, 2014

(51) Int. Cl.
*A61B 5/055* (2006.01)
*G01R 33/48* (2006.01)
*A61N 5/10* (2006.01)
*G01R 33/3873* (2006.01)

(52) U.S. Cl.
CPC ............ *A61B 5/055* (2013.01); *A61N 5/1049* (2013.01); *G01R 33/4808* (2013.01); *A61N 5/1045* (2013.01); *A61N 2005/1055* (2013.01); *A61N 2005/1094* (2013.01); *G01R 33/3873* (2013.01)

(58) Field of Classification Search
CPC .... A61B 5/055; A61N 5/1049; A61N 5/1045; A61N 2005/1055; A61N 2005/1094; G01R 33/4808; G01R 33/3873
See application file for complete search history.

(56) References Cited

U.S. PATENT DOCUMENTS

| 6,891,375 | B2* | 5/2005 | Goto et al. | 324/320 |
| 2006/0193441 | A1* | 8/2006 | Cadman | 378/153 |
| 2010/0322497 | A1* | 12/2010 | Dempsey | G01R 33/4826 382/131 |
| 2011/0012593 | A1* | 1/2011 | Shvartsman et al. | 324/307 |
| 2011/0121832 | A1* | 5/2011 | Shvartsman et al. | 324/318 |
| 2013/0296687 | A1* | 11/2013 | Dempsey | A61N 5/1049 600/411 |
| 2014/0084926 | A1* | 3/2014 | Amthor et al. | 324/309 |

(Continued)

FOREIGN PATENT DOCUMENTS

| CN | 1394550 | A | 2/2003 |
| CN | 101309726 | A | 11/2008 |
| CN | 102247658 | A | 11/2011 |
| CN | 102472830 | A | 5/2012 |
| CN | 102713682 | A | 10/2012 |
| EP | 2 359 905 | A1 | 8/2011 |
| GB | 2 393 373 | A | 3/2004 |
| WO | WO 03/008986 | A2 | 1/2003 |
| WO | WO-2007/012933 | A2 | 2/2007 |
| WO | WO-2011/008969 | A1 | 1/2011 |
| WO | WO-2011/063342 | A1 | 5/2011 |
| WO | WO 2012164527 | A1 * | 12/2012 |
| WO | WO 2015/085008 | | 6/2015 |
| WO | WO 2015085008 | A1 * | 6/2015 ........... G06T 7/0026 |

OTHER PUBLICATIONS

St. Aubin et al., "Magnetic decoupling on the linac in a low field biplanar linac-MR system", Med. Phys. 37 (9), Sep. 2010, pp. 4755-4761.*
Lagendijk J. J. et al. "MRI guided radiotherapy: A MRI based linear accelerator." Radiotherapy & Oncology. vol. 56, No. Supplement 1. Sep. 2000. (Sep. 2000):S60-S61. XP008012866. 19th Annual Meeting of the European Society for Therapeutic Radiology and Oncology. Istanbul, Turkey; Sep. 19-23, 2000.
Lagendijk, Jan J.W. et al. "MRI/linac integration." *Radiotherapy and Oncology*. vol. 86 No. 1. (Nov. 26, 2007):25-29.
Overweg, J. et al. "System for MRI guided Radiotherapy." *Proc. Intl. Soc. Mag. Reson. Med.* 17(Apr. 18, 2009):594.

*Primary Examiner* — Long V Le
*Assistant Examiner* — Colin T Sakamoto
(74) *Attorney, Agent, or Firm* — Mintz Levin Cohn Ferris Glovsky and Popeo, P.C.

(57) ABSTRACT

Systems and methods for delivery of radiotherapy in conjunction with magnetic resonance imaging in which various conductors, shields and shims may be used to solve issues occurring when radiation therapy equipment is placed in the vicinity of an magnetic resonance imaging system.

18 Claims, 7 Drawing Sheets

(56) References Cited

U.S. PATENT DOCUMENTS

| | | | | |
|---|---|---|---|---|
| 2014/0121495 A1* | 5/2014 | Dempsey | A61N 5/1064 | 600/411 |
| 2014/0263990 A1* | 9/2014 | Kawrykow | A61N 5/1031 | 250/252.1 |
| 2014/0266206 A1* | 9/2014 | Dempsey | G01R 33/34092 | 324/322 |
| 2014/0266208 A1* | 9/2014 | Dempsey | A61N 5/1049 | 324/322 |
| 2014/0330108 A1* | 11/2014 | Dempsey | A61N 5/1045 | 600/411 |
| 2014/0347053 A1* | 11/2014 | Dempsey | A61B 5/055 | 324/318 |
| 2015/0065860 A1* | 3/2015 | Shvartsman | G01R 33/3806 | 600/411 |
| 2015/0077118 A1* | 3/2015 | Shvartsman | G01R 33/385 | 324/322 |
| 2015/0154756 A1* | 6/2015 | Gerganov | G06T 7/32 | 382/131 |
| 2015/0165233 A1* | 6/2015 | Dempsey | A61N 5/1045 | 250/492.1 |
| 2015/0185300 A1* | 7/2015 | Shvartsman | G01R 33/3642 | 324/322 |

* cited by examiner

SYSTEMS AND METHODS FOR RADIOTHERAPY WITH MAGNETIC RESONANCE IMAGING

TECHNICAL FIELD

The present disclosure relates to systems and methods for the delivery of radiotherapy in conjunction with magnetic resonance imaging.

BACKGROUND

It is desirable to combine radiation therapy with repetitive real-time imaging using a magnetic resonance imaging system (MRI) in order to better locate and treat therapy targets while sparing nearby healthy tissue. While MRIs and radiation treatment systems such as linear accelerators or radioisotope beams have operated separately from one another for quite some time, combining the two technologies presents many significant technological challenges. Examples of such challenges include the magnetic fields and eddy currents generated in ferromagnetic and conductive radiotherapy equipment through the MRI's main and gradient magnets, both of which can destroy an MRI's ability to provide quality images.

SUMMARY

Disclosed herein are systems and methods for combining radiotherapy with magnetic resonance imaging.

In one embodiment, a system may include a magnetic resonance imaging system, a gantry, one or more radiation therapy heads fixed to the gantry, one or more collimating devices associated with the one or more heads, including a plurality of leaves, one or more leaf drive motors for moving the leaves, the one or more leaf drive motors including one or more position sensors, and a magnetic shield substantially surrounding the one or more position sensors, one or more permanent magnets adjacent the one or more leaf drive motors, the one or more permanent magnets oriented so as to counteract the MRI's main magnetic field, and one or more additional conductive elements disposed around the gantry in a substantially symmetrical manner. The one the one or more additional conductive elements may have a shape, volume or material permeability designed to substantially match the shape, volume or material permeability of the collimating devices. In addition, the one or more additional conductive elements may be substantially similar to the outer housings of the collimating devices. In one embodiment, only one radiation therapy head is fixed to the gantry and only one collimating device is associated with the one radiation therapy head and the one or more additional conductive elements is a single conductive element extending substantially around the portion of the gantry not occupied by the one collimating device. Furthermore, the magnetic shield may be made of steel and may be cylindrical in shape.

In another embodiment, a system may include a magnetic resonance imaging system, a gantry, one or more radiation therapy heads fixed to the gantry, one or more collimating devices associated with the one or more heads and one or more additional conductive elements disposed around the gantry in a substantially symmetrical manner. The one or more additional conductive elements may be additional collimating devices or may be substantially similar to the outer housings of the collimating devices. In addition, the one or more additional conductive elements may have a shape, volume or material permeability designed to substantially match the shape, volume or material permeability of the collimating devices. In another embodiment, the one or more radiation therapy heads may be three radioisotopic sources, and the one or more additional conductive elements may be three conductors substantially similar to the outer housings of the collimating devices. In yet another embodiment, only one radiation therapy head is fixed to the gantry and only one collimating device is associated with the one radiation therapy head and the one or more additional conductive elements comprises a single conductive element extending substantially around the portion of the gantry not occupied by the one collimating device.

In still another embodiment, the system may include a magnetic resonance imaging system, a gantry, one or more radiation therapy heads fixed to the gantry, one or more collimating devices associated with the one or more heads, including a plurality of leaves, one or more leaf drive motors for moving the leaves, the one or more leaf drive motors including one or more position sensors and a magnetic shield substantially surrounding the one or more position sensors. The magnetic shield may have a cylindrical shape and may be made out of ferromagnetic material, such as steel.

In another embodiment, the system may include a magnetic resonance imaging system, a gantry, one or more radiation therapy heads fixed to the gantry, one or more collimating devices associated with the one or more heads, including a plurality of leaves, one or more leaf drive motors for moving the leaves and one or more permanent magnets adjacent the one or more leaf drive motors, the one or more permanent magnets oriented so as to counteract the MRI's main magnetic field. Permanent magnets may be placed on either side of the one or more leaf drive motors and may be made from Neodymium.

These and other features, aspects, and advantages of the present disclosure will become better understood with reference to the following description and claims.

BRIEF DESCRIPTION OF DRAWINGS

Features, aspects, and implementations of the disclosure are described in conjunction with the attached drawings, in which.

DETAILED DESCRIPTION

Figure 1:
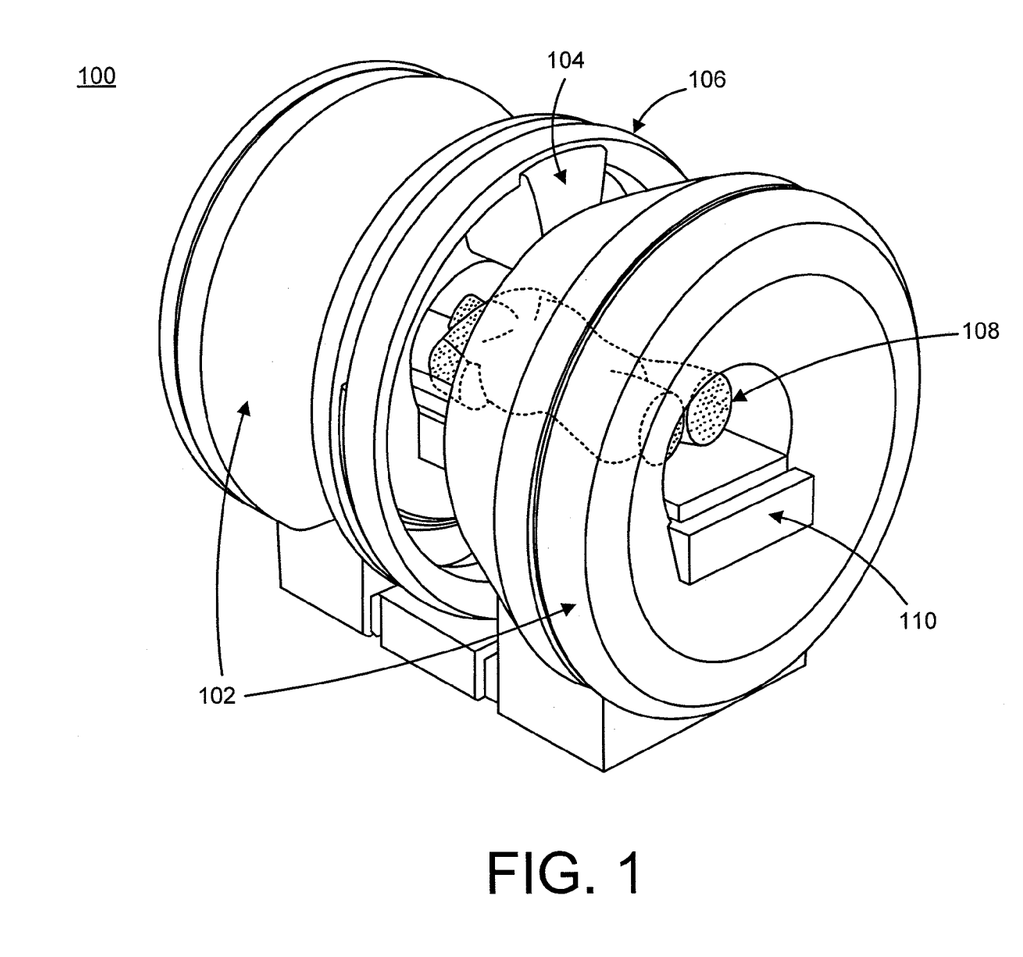
FIG. 1 is a simplified diagram illustrating aspects of a radiation therapy device operating in conjunction with a magnetic resonance imaging system consistent with implementations of the current subject matter.

Disclosed herein are systems and methods for combining radiotherapy with magnetic resonance imaging. FIG. 1 is a simplified schematic view of an implementation of a radiation therapy system including a radiation therapy head 104 mounted on a gantry 106, which can rotate to different positions to enable radiation delivery from different angles. The exemplary system depicted in FIG. 1 also includes an MRI 102, which may be used for real-time imaging during radiation therapy and may be of the split or open type of MRI as shown. Radiation therapy head 104 can be used to direct a treatment beam at a target within patient 108 lying on couch 110.

Figure 2:
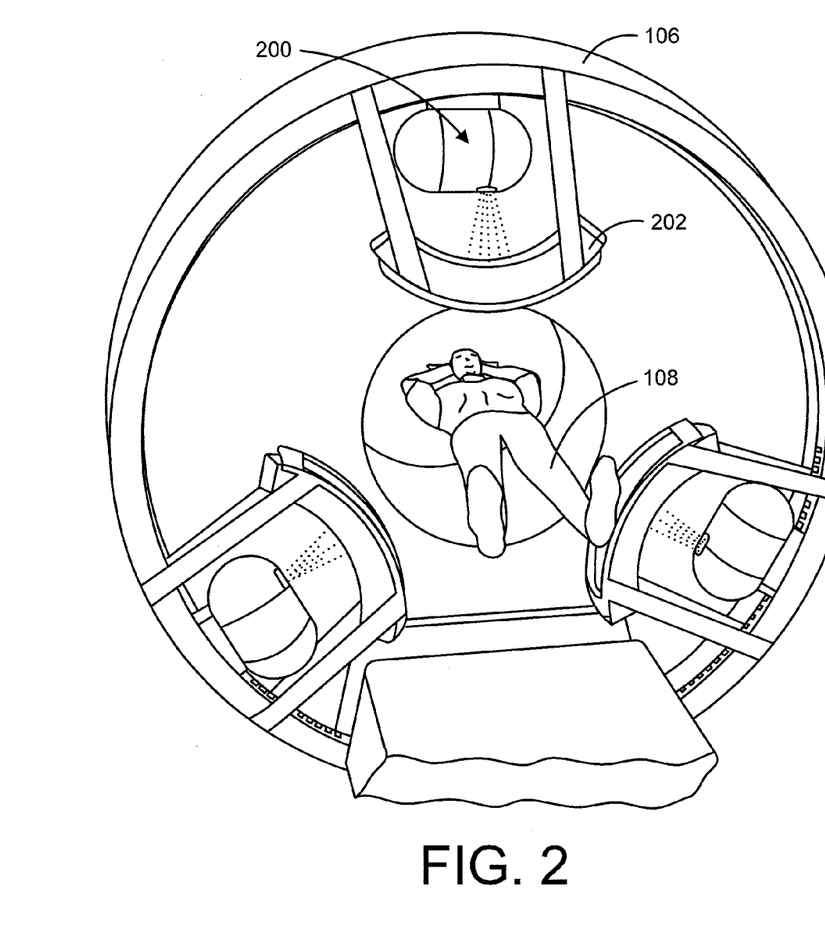
FIG. 2 is a simplified diagram illustrating an example of a treatment system consistent with implementations of the current subject matter.

FIG. 2 depicts an example of a radiation therapy system that may be used with the disclosed systems and methods. The example depicted includes three radioisotopic sources 200, such as Cobalt-60, mounted on gantry 106, directing three radiotherapy beams at patient 108. While this example utilizes radioisotopic beams, this disclosure contemplates and is applicable to other radiotherapy beam types such as linear accelerators, proton beams, etc. In addition, while the example of FIG. 2 shows three radiotherapy heads spaced in an equidistant manner around the gantry, the systems and methods disclosed herein apply to any number of radiotherapy heads (i.e., one or more).

FIG. 2 also depicts collimating devices 202 attached to gantry 106 and associated with each of the sources 200. Collimating devices 202 may, for example, be multi-leaf collimators (MLCs), as shown in further detail in FIG. 3. MLCs typically have two banks of opposing pairs of leaves 302, which move independently and can open to form apertures of various shapes and sizes. The number of leaves 302 can vary. Leaves 302 may be made of tungsten or any suitable material or materials for blocking radiation. MLCs may also employ a tongue and groove arrangement on the long sides and front of the leaves 302 to limit interleaf radiation leakage and can be configured for inter-digitation of the leaves 302 in the closed position.

Figure 3:
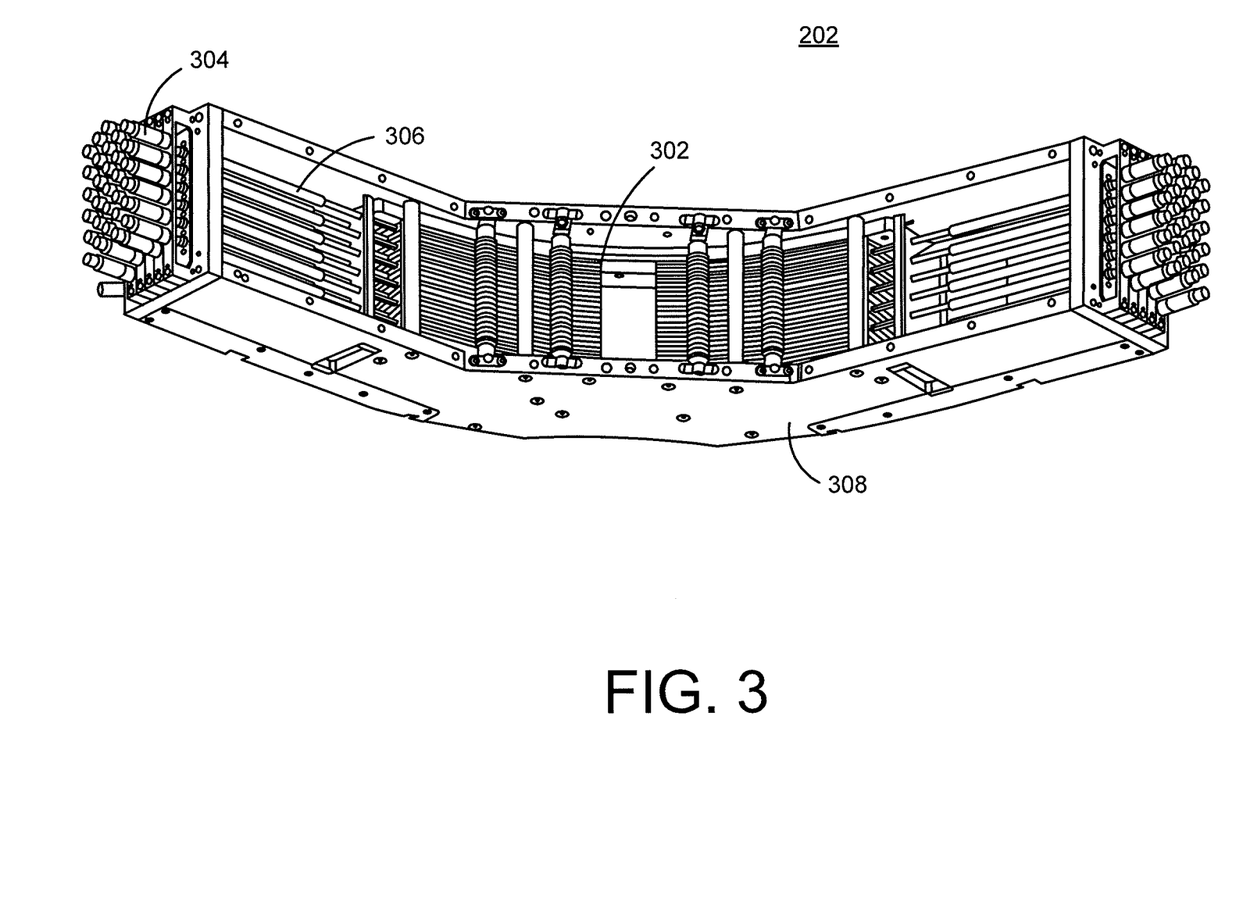
FIG. 3 illustrates an exemplary collimating device, specifically a multi-leaf collimator.

Each leaf 302 of each bank of leaves may be capable of independent motion and may be driven by leaf motors 304 through connecting rods 306. An MLC control system can control the two opposing banks of leaves 302 to independently position the edge of each leaf 302 to a specified location in order to block a radiation beam and form a field size of a specific shape.

The MLC leaves 302, motors 304, and other components may be supported by housing 308 that then attaches to gantry 106. Housing 308 may be, for example, made from aluminum.

Figure 4A:
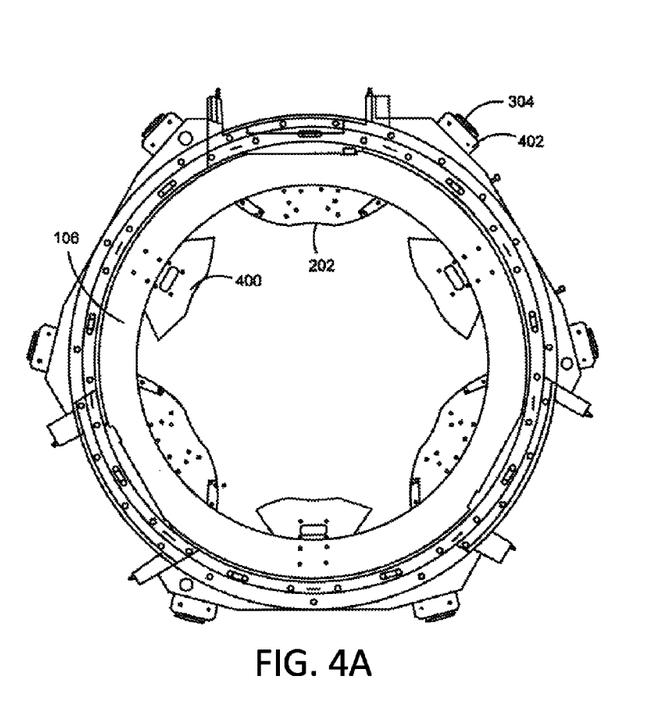
FIG. 4A illustrates one example of an arrangement of conductive elements consistent with implementations of the current subject matter.

FIG. 4A depicts an exemplary gantry 106 layout for the example radiation therapy system depicted in FIG. 2 having three radioisotopic sources 200 along with three corresponding collimating devices 202. The embodiment of FIG. 4A further includes additional conductive elements 400. Conductive elements 400 may be made of a single material or combine multiple materials. The conductive elements preferably have a shape, volume and material permeability (i.e., the degree of magnetization that a material obtains in response to an applied magnetic field) designed to substantially match those of collimating devices 202 in such respects as are pertinent to the generation of eddy currents during energizing of the MRI's gradient coils. For example, in the embodiment depicted in FIG. 4A, conductive elements 400 could comprise identical multi-leaf collimators.

Because including additional sets of identical multi-leaf collimators would be expensive, and because eddy currents are primarily generated in the outer housings 308 of collimating devices 202, conductive elements 400 may merely be substantially similar to the housings 308 of collimating devices 202. For example, conductive elements 400 may be pairs of aluminum multi-leaf collimator housings. Alternatively, conductive elements 400 may be other shapes or other materials that substantially mimic the eddy current properties of the collimating devices 202 or housings 308.

Figure 4B:
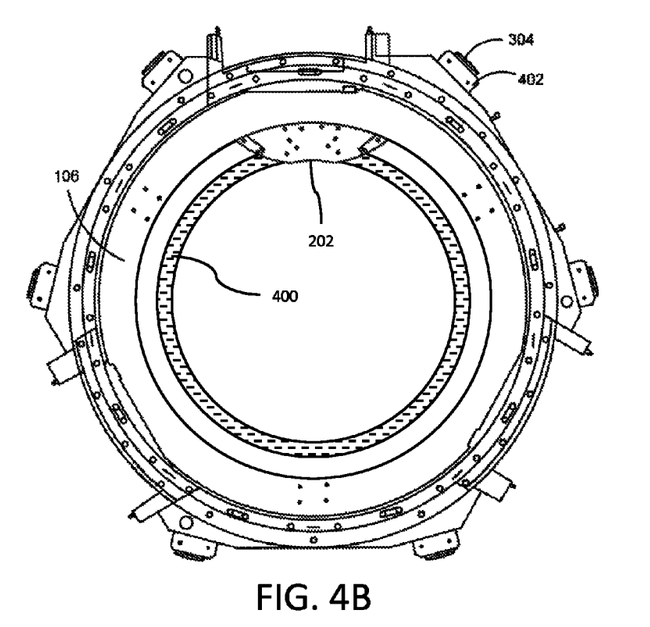
FIG. 4B illustrates an example of an arrangement of one collimating device and one conductive element consistent with implementations of the current subject matter.

Conductive elements 400 are preferably placed in positions around gantry 106 to create a substantially symmetrical pattern, as depicted in FIG. 4A. The positions and number of conductive elements 400 may vary, but the resulting arrangement is preferably symmetrical about the circumference of gantry 106. As noted above, this disclosure contemplates and is applicable to any type of radiotherapy device. In the case where there is a single radiation therapy head, for example, a linear accelerator, the same principles for the additional conductive elements 400 described above apply. In one example, there may be five conductive elements 400 substantially equally spaced around gantry 106, along with the single collimating device 202. In another example, a single conductive element 400 may extend around substantially the entire portion of the circumference of gantry 106 not occupied by collimating device 202, for example as shown in FIG. 4B. While a number of examples have been given for the design and layout of conductive elements 400, any design and layout meeting the spirit of this disclosure is contemplated.

Figures 5A, 5B:
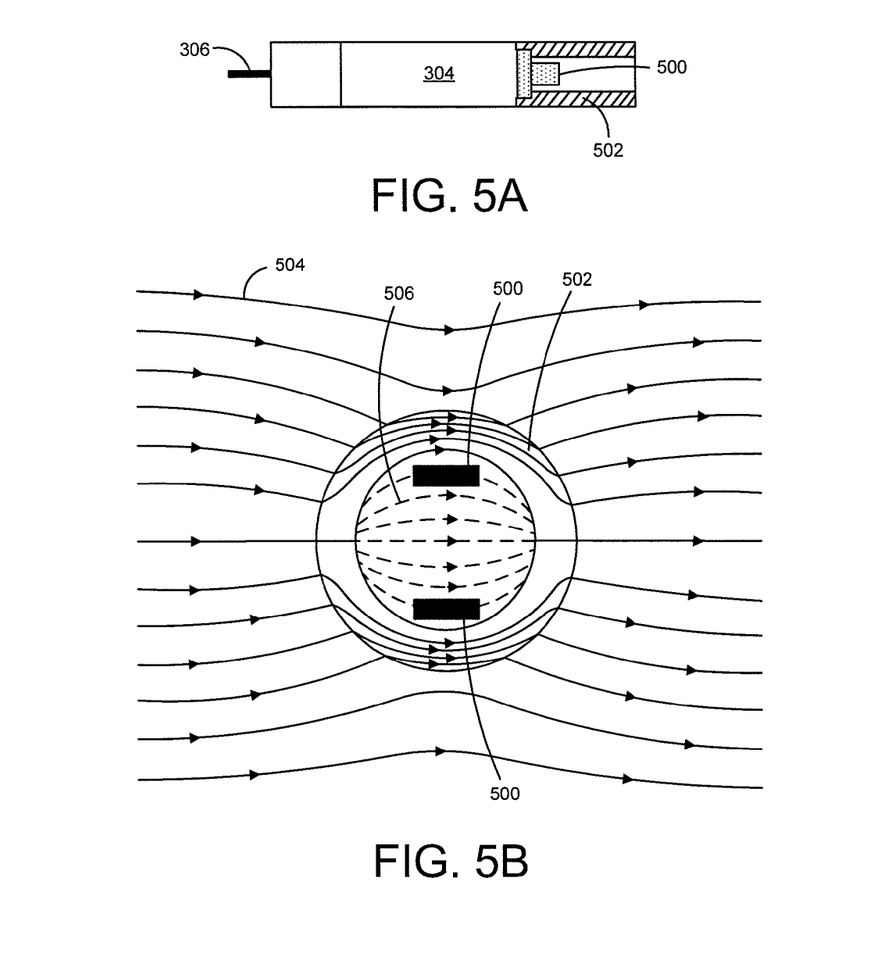
FIG. 5A is a simplified diagram illustrating a leaf motor combined with an example magnetic shield consistent with implementations of the current subject matter.
FIG. 5B is a simplified representation of the effect of a magnetic shield on an MRI's main magnetic field.

Leaf motors 304 associated with collimating devices 202, typically include one or more position sensors 500 capable of determining the position of associated leaves 302, as shown in FIG. 5A. For example, position sensor 500 may be a Hall effect encoder, which is capable of determining how many times a motor has rotated. A preferred embodiment includes magnetic shields 502 substantially surrounding sensors 500. Magnetic shield 502 is preferably cylindrically shaped and made of a ferromagnetic material, in one example. One such ferromagnetic material may be steel, but other materials and shapes suitable for magnetic shielding can be used. In one embodiment, the wall thickness of a steel cylinder is in the range of 1.5-2.0 mm and reduces the magnetic field within the shield to below 140 Gauss. In one preferred embodiment, the wall thickness of the steel cylinders 1.6 mm. FIG. 5B demonstrates how magnetic shield 502 can decrease the magnetic field to which sensor 500 is objected from that of the main magnet magnetic field 504 to a reduced magnetic field 506 observed within the shield.

Position sensors 500 are preferably oriented within magnetic shield 502 so as to be in the location at which the magnetic field is weakest, as shown in FIG. 5B as the top and bottom of magnetic shield 502.

Figure 6:
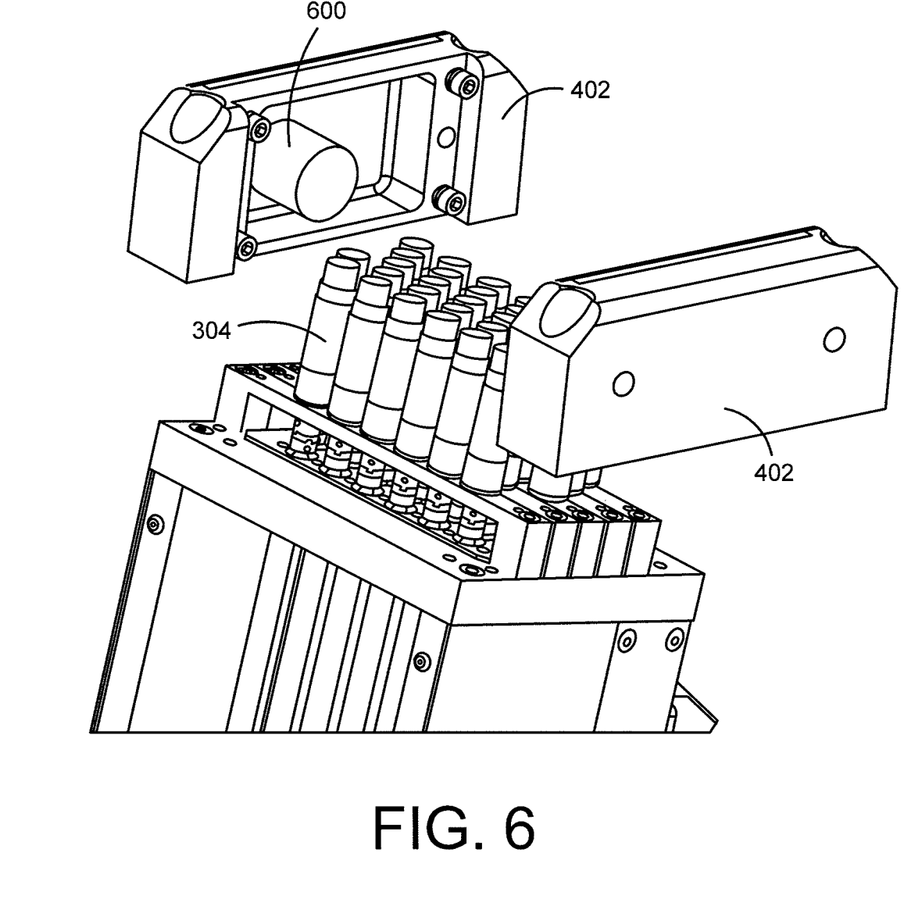
FIG. 6 is a simplified illustration of permanent magnets being placed adjacent a bank of leaf motors consistent with implementations of the current subject matter; and, FIG. 7 illustrates an exemplary magnetic orientation of permanent magnets with respect to an MRI's main magnetic field consistent with implementations of the current subject matter.
Figure 7:
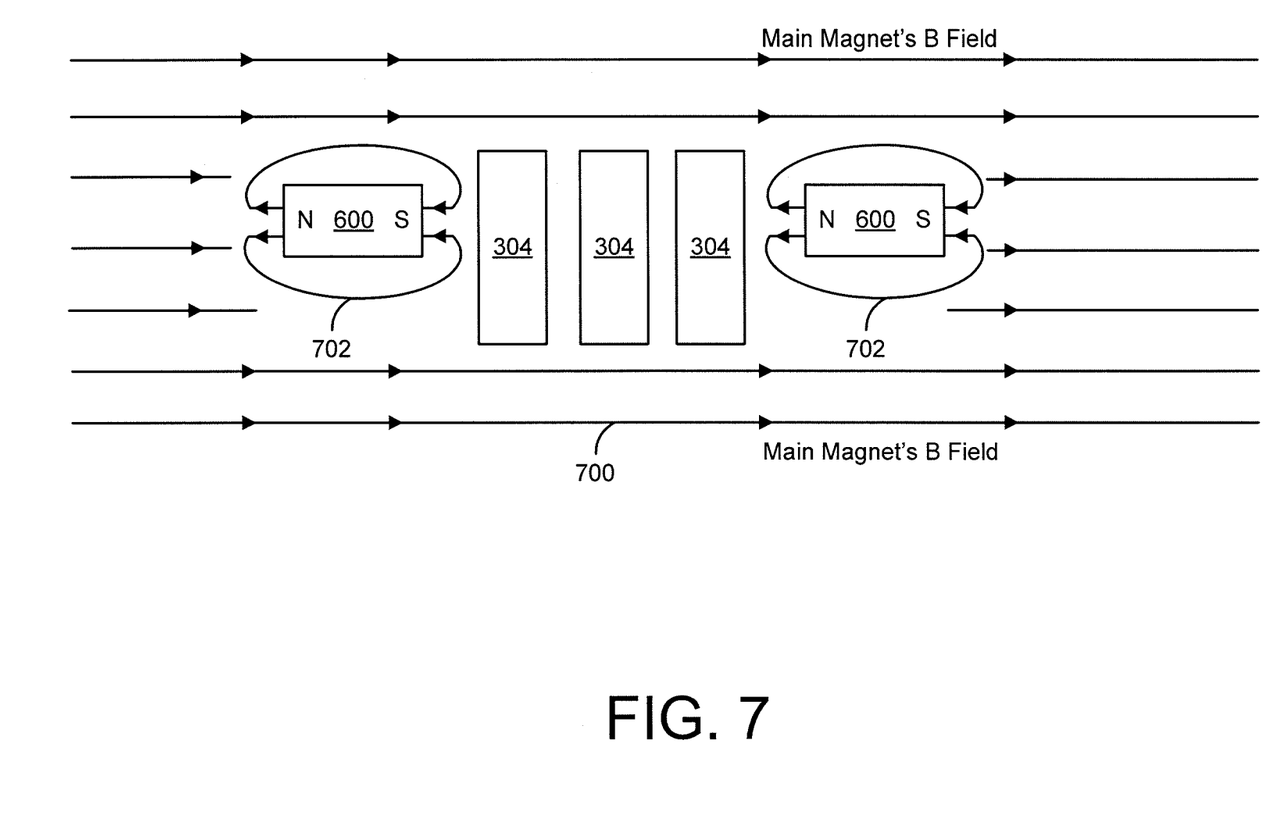

In one embodiment of the disclosure, permanent magnets 600 may be placed adjacent to the bank of motors 304, as shown in FIG. 6. Permanent magnets 600 may be held in place by housings 402 and, in one embodiment, may be made from Neodymium (NdFeB). The polar orientation of the permanent magnets 600 should be such that it counteracts the MRI's main magnetic field and the magnetic field induced in the motors and motor shields 304. FIG. 7 illustrates this orientation of permanent magnets 600 amidst the MRI's main magnetic field 700, showing the north-south polarity of permanent magnets 702 opposing the main magnet's magnetic field 700.

One embodiment of the disclosure contemplates one permanent magnet being placed on either side of the bank of motors 304 as shown in FIG. 6. However, any number and arrangement of properly oriented permanent magnets 600 may be used that results in substantial cancellation of the magnetic field induced in motor shields 304 and other ferromagnetic materials in the area (for example, the motor housings). As an alternative to permanent magnets 600, active windings could be used as well. The canceling effect of the magnet design's strengths, field orientations, and locations can be determined utilizing modeling software such as FARADAY, available from Integrated Engineering Software, or any other appropriate software such as VectorField, for example, and with further analysis of results potentially being performed in a program such as MATLAB or any other appropriate software such as FORTRAN, for example.

In one embodiment of the systems and methods of the disclosure, the leaf motors 304 may also be oriented so that the permanent magnets stators within them either cancel out the group of motors' magnetic field, or may alternatively be oriented in a manner that causes the group's magnetic field to be known or predictable.

While placing permanent magnets 600 adjacent the banks of leaf motors 304 substantially improves field homogeneity, the main magnetic field can be further improved, and the effect of radiation therapy equipment on MRI 102 further decreased. In addition to the leaf motors 304, magnetic shields 502, motor housings, stators within the motors and the like, the collimating devices 202 contain leaves 302 that may also have ferromagnetic properties. For example, leaves 302 may be made from a material such as tungsten, which has a relatively low permeability of approximately 1.03, but which, due to the large volume of the leaves, may also have a significant effect on the MRI's magnetic field. Magnetic field homogeneity may be in further improved, for example, by placing additional permanent magnet shims within the system. For example, in the embodiment depicted in FIG. 4A and discussed above, additional permanent magnets may be placed on the three conductive elements 400. While such location has proven beneficial for this embodiment, there are numerous other locations that would prove beneficial to field homogeneity, as can be determined using modeling software such as FARADAY or any other appropriate software such as VectorField, for example. Other locations could include, for example, on the collimating devices 202 themselves. In addition, active windings could be used in place of, or in conjunction with, the permanent magnets. Finally, standard ferromagnetic shims may be used.

While various implementations in accordance with the disclosed principles have been described above, it should be understood that they have been presented by way of example only, and are not limiting. Thus, the breadth and scope of the invention(s) should not be limited by any of the above-described exemplary implementations, but should be defined only in accordance with the claims and their equivalents issuing from this disclosure. The present disclosure contemplates that the calculations disclosed in the implementations herein may be performed in a number of ways, applying the same concepts taught herein, and that such calculations are equivalent to the implementations disclosed. Furthermore, the above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system comprising:
   a magnetic resonance imaging system;
   a gantry having a circumference around a patient couch within the magnetic resonance imaging system;
   a radiation therapy head fixed to the gantry;
   a collimating device associated with the head, including a plurality of leaves;
   a leaf drive motor for moving the leaves, the leaf drive motor including one or more position sensors, and a magnetic shield substantially surrounding the one or more position sensors;
   a permanent magnet adjacent the leaf drive motor, the permanent magnet oriented so as to counteract a main magnetic field of the magnetic resonance imaging system; and
   a conductive element disposed around the gantry such that the conductive element and the radiation therapy head are arranged in a substantially symmetrical pattern about the circumference of the gantry.

2. The system of claim 1 wherein the collimating device has a shape, a volume, and a material permeability, and the conductive element matches at least one of the shape, the volume, and the material permeability of the collimating device.

3. The system of claim 1 wherein the collimating device includes a housing and the conductive element is substantially similar to the housing of the collimating device.

4. The system of claim 1 wherein the radiation therapy head is fixed to the gantry and conductive element is a single conductive element extending substantially around a portion of the gantry not occupied by the collimating device.

5. The system of claim 1 wherein the magnetic shield comprises steel and has a cylindrical shape.

6. A system comprising:
   a magnetic resonance imaging system;
   a gantry having a circumference around a patient couch within the magnetic resonance imaging system;
   a radiation therapy head fixed to the gantry;
   a collimating device associated with the head, the collimating device comprising:
   a housing;
   multi-leaf collimator leaves; and
   multi-leaf collimator motors; and
   a conductive element disposed around the circumference to form a substantially symmetrical pattern with the collimating device, the conductive element shaped substantially similar to the housing and constructed from a material which, in combination with the shape of the conductive element, substantially mimics eddy-current properties of the collimating device, wherein the conductive element is not a duplicate of the collimating device.

7. The system of claim 6 wherein the conductive element comprises an additional collimating device.

8. The system of claim 6 wherein the collimating device has a shape, a volume, and a material permeability, and the conductive element matches at least one of the shape, the volume, and the material permeability of the collimating device.

9. The system of claim 6 further comprising:
two additional radiation therapy heads, each of which comprises a radioisotopic source;
two additional collimating devices, each of which is associated with one of the two additional radiation therapy heads, and each of which includes an additional housing; and
two additional conductive elements, each of which is associated with one of the two additional radiation therapy heads, and each of which comprises a conductor substantially similar to the additional housing of the two additional collimating devices; and
wherein the substantially symmetrical pattern includes the collimating device, the two additional collimating devices, the conductive element, and the two additional conductive elements arranged substantially symmetrically around the circumference of the gantry.

10. The system of claim 6 wherein the radiation therapy head is fixed to the gantry and the conductive element is a single conductive element extending substantially around a portion of the gantry not occupied by the collimating device.

11. The system of claim 6 further comprising:
a plurality of radiation therapy heads, wherein the radiation therapy head is included in the plurality of radiation therapy heads;
a plurality of collimating devices, wherein:
the collimating device is included in the plurality of collimating devices,
each of the plurality of collimating devices is associated with one of the plurality of radiation therapy heads, and
each of the plurality of collimating devices includes a housing; and
a plurality of conductive elements, wherein:
each of the plurality of conductive elements is associated with one of the plurality of radiation therapy heads, and
each of the plurality of conducting elements comprise conductor substantially similar to the housing of the associated collimating device; and
wherein the substantially symmetrical pattern about the circumference of the gantry includes the plurality of conductive elements and the plurality of collimating devices arranged in the substantially symmetrical pattern.

12. A system comprising:
a magnetic resonance imaging system;
a gantry;
one or more radiation therapy heads fixed to the gantry;
one or more collimating devices associated with the one or more heads, including a plurality of leaves;
a plurality of leaf drive motors for moving the leaves, each of the plurality of leaf drive motors including at least one position sensor; and
a plurality of magnetic shields for each of the plurality of leaf drive motors, each magnetic shield substantially surrounding the at least one position sensor of one of the plurality of leaf drive motors.

13. The system of claim 12 wherein the plurality of magnetic shields have a cylindrical shape.

14. The system of claim 12 wherein the plurality of magnetic shields comprise a ferromagnetic material.

15. The system of claim 14 wherein the ferromagnetic material comprises steel.

16. A system comprising:
a magnetic resonance imaging system;
a gantry;
one or more radiation therapy heads fixed to the gantry;
one or more collimating devices associated with the one or more heads, including a plurality of leaves;
one or more leaf drive motors for moving the leaves; and,
one or more permanent magnets adjacent the one or more leaf drive motors, the one or more permanent magnets oriented so as to counteract the MRI's main magnetic field.

17. The system of claim 16 wherein the one or more permanent magnets comprises permanent magnets placed on opposite sides of the one or more leaf drive motors.

18. The system of claim 16 wherein the one or more permanent magnets comprise Neodymium.

* * * * *